United States Patent [19]

Mark et al.

[11] Patent Number: 4,740,220
[45] Date of Patent: Apr. 26, 1988

[54] DUST DETECTION

[75] Inventors: David Mark, Stow; Gordon Lynch; Harold Gibson, both of Edinburgh; James H. Vincent, Haddington, all of Scotland

[73] Assignee: Coal Industry (Patents) Ltd., United Kingdom

[21] Appl. No.: 888,165

[22] Filed: Jul. 22, 1986

[30] Foreign Application Priority Data

Aug. 23, 1985 [GB] United Kingdom ............... 8521220

[51] Int. Cl.4 ............................................. B01D 50/00
[52] U.S. Cl. ....................................... 55/270; 55/325; 55/332; 55/439; 55/446; 73/863.22
[58] Field of Search ............... 55/270, 325, 326, 332, 55/321, 439, 446, 467; 73/863.22, 863.23, 28

[56] References Cited

U.S. PATENT DOCUMENTS 3,693,457  9/1972  Pilat ...................................... 73/28 X
3,795,135  3/1974  Andersen ............................... 73/28
3,953,182  4/1976  Roth ................................. 55/446 X
3,983,743  10/1976  Olin et al. ......................... 55/270 X
4,189,937  2/1980  Nelson ............................. 55/270 X
4,327,594  5/1982  Nelson ........................... 73/863.22

Primary Examiner—Kathleen J. Prunner
Attorney, Agent, or Firm—Stevens, Davis, Miller & Mosher

[57] ABSTRACT

A personal dust spectrometer for aerodynamically classifying and collecting sub-fractions of inspirable dust, has an entry which has an entry efficiency approximating that of the human head during inhalation, and a cascade impactor comprising a stack of stages each having a flat element and a peripheral wall and gas exit holes. A connector enables a gas sampling pump to be attached to draw air through the entry and through the cascade impactor. A filter is desirably used to collect the smallest dust particles. All the dust entering the device is collected and is measurable.

6 Claims, 2 Drawing Sheets

DUST DETECTION

This invention concerns improvement in dust detection, and more especially it concerns a personal inspirable dust spectrometer.

BACKGROUND OF THE INVENTION

We have described an inspirable (previously referred to as "inhalable") dust spectrometer in Published UK Patent Application No. 2,129,335A. The device described specifically therein, however, is not easily adaptable to miniaturization to produce a personal spectrometer capable of being carried continuously by a wearer and giving a representative picture of the exposure of the wearer to dust. Personal dust samplers are known and some are currently marketed, but in general these provide only a limited amount of information on dust collected during a sampling period, often solely a weight of so-called "total" or "respirable dust" collected. There are a few small cascade impactors commerically available and which do fractionate dust sampled, but none incorporates features yielding an inspirable dust fraction, and although these can be carried on the body as personal samplers, they also tend to be very expensive. It is an aim of the present invention to provide a personal dust sampler which selects an inspirable fraction of airborne dust and then collects a number of sub-fractions thereof from which biologically-relevant information can be obtained.

SUMMARY OF THE INVENTION

The present invention provides a personal inspirable dust spectrometer comprising an inlet section having an entry which when worn on the body, has an entry efficiency for airborne dust approximating to that of the human head during inhalation, and, connected to said inlet section, a multi-stage cascade impactor having an inlet and an outlet and having a series of stages each capable of collecting a sub-fraction of dust and comprising a generally flat element with a peripheral wall and at least one gas exit hole in the flat element, said stages being dismountably assembled so as the peripheral wall of one stage seals by contacting the base of the stage immediately before, and the gas exit hole(s) from one stage are positioned to permit gas flow to impinge on a part of the flat element of the succeeding stage, and connected to the outlet of the impactor, means for drawing gas through the entry and through the impactor. Desirably, a filter is included between the outlet of the impactor and the means for drawing gas.

It is preferred to use as the entry an aperture surrounded by a lip; this may be formed by a dismountably entry having an entry portion protruding through an aperture in the inlet section. The lip suitably protrudes about 1–2 mm beyond the surrounding part of the inlet section. It is not known whether or not the shape of the entry is critical; however, a circular entry of about 15 mm diameter has been found to give accpetable results at a standard gas flow rate of 2 l/min.

A cascade impactor of 4–10 stages is preferred. Each stage is conveniently essentially the same shape, although the peripheral walls may vary in size, and the exit holes are progressively reduced in size from the inlet to the outlet end. Since the gas flow through each exit hole must impinge on part of the succeeding stage, the axial position of the holes must be staggered. These may conveniently be from 1 to 8 exit holes per stage; preferaby, however, each stage should have an identical number of exit holes, and preferably these are located symmetrically. Preferably, the stages are constructed and assembled so that the areas of impingement lie on the same radius as and equidistant from the exit holes.

Preferably, the cascade impactor is of circular section and each disc is a disc with a peripheral wall. Preferably each disc seals with the preceding stage by means of an O-ring recessed into the base of the preceding stage.

The design of the cascade impactor permits each stage to be dismounted and weighed, and there is no part of the cascade impactor which is exposed to dust-laden air other than a stage including its wall and base. Thus, there can be no "wall-losses", that is, all the dust which enters the impactor and contacts part of a stage is eventually included in the weighing process, unlike many cascade impactors in which "wall-losses" of up to 30% in certain particle size ranges have been found.

BRIEF DESCRIPTION OF THE DRAWINGS

The invention will now be described by way of example, with reference to the accompanying drawings in which.

Figure 1:
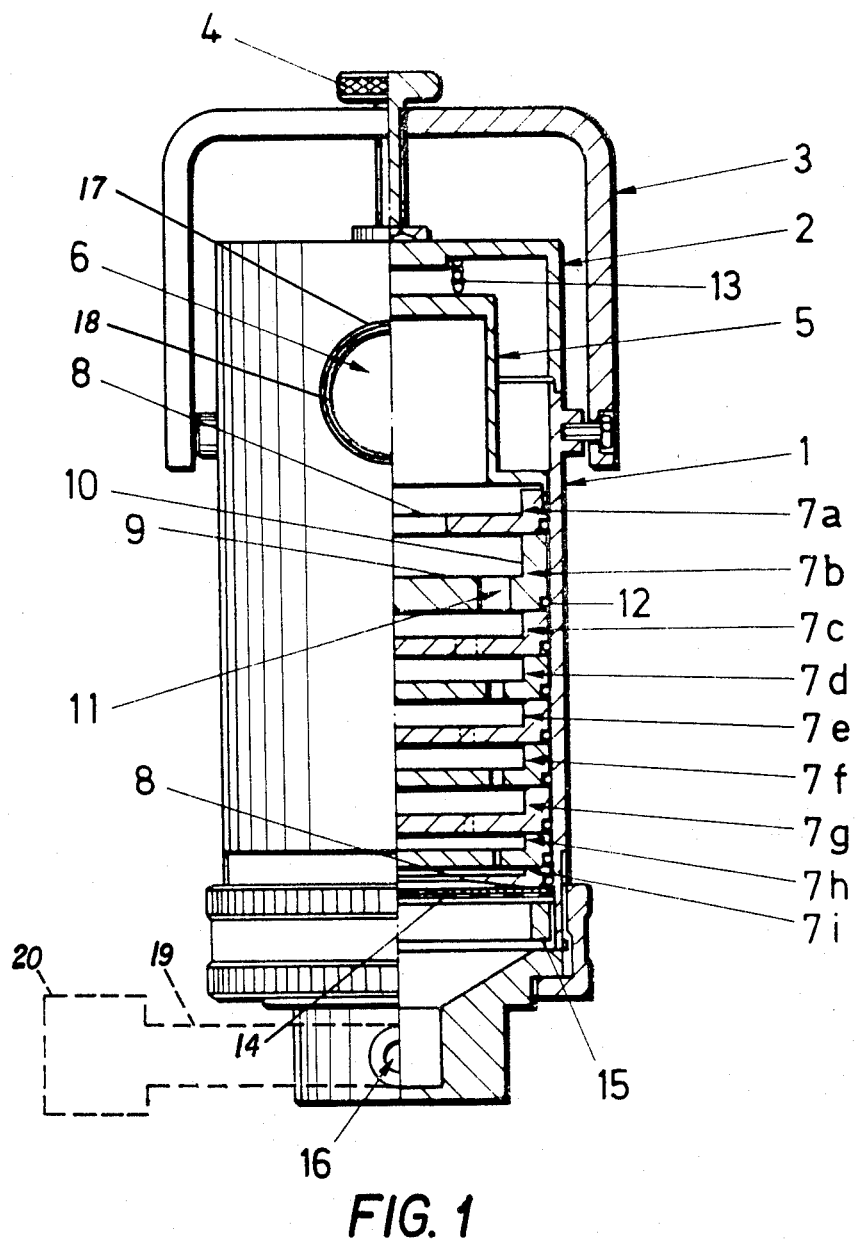
FIG. 1 is a front view partly in section of a spectrometer according to the invention.
Figure 2:
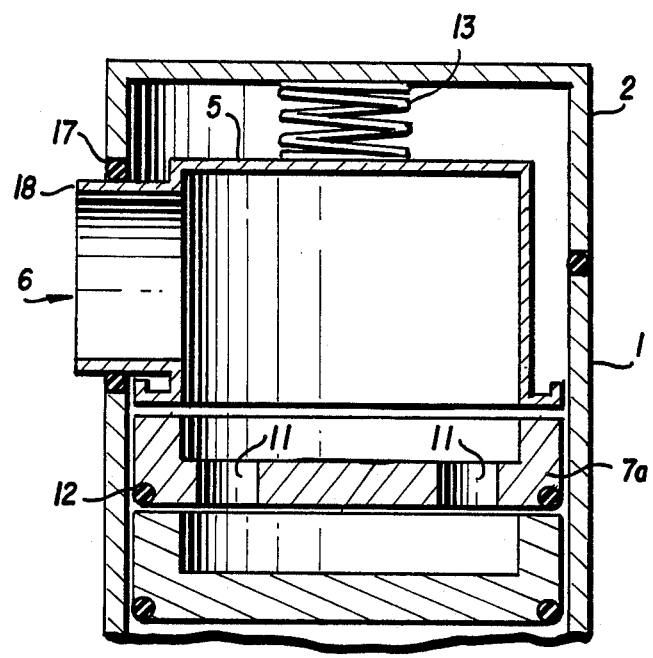
FIG. 2 is a right side cross sectional view of the top portion of FIG. 1 taken along the vertical centerline of the inlet aperture.

The spectrometer has a cylindrical impactor body, 1. Releasably mounted on top of cylinder or casing 1 is an inlet housing, 2, which is held onto the cylinder by means of a yoke 3, with a screw clamp, 4. The inlet housing has an inlet aperture 17 and dismountably held within the housing is an entry, 5, having a circular entry aperture, 6, and an open base. The entry has an entry portion which protrudes 1.5 mm beyond the inlet housing on its central line to form a lip 18. The base edge of the entry contacts the first of a stack of eight impactor stages, 7, (a–h). The first stage, 7a, has a single central gas exit hole, 8. The other stages consist of a series of cup shaped bodies each having a disc portion, 9, and an upstanding wall portion, 10, and having four gas exit holes, 11. Each stage has a pin and socket locating device (not shown) to ensure its correct orientation and positioning with respect to its neighbors. The exit holes are symmetrically positioned and aligned mid way between the exit holes on neighboring stages. Below the final stage 7h is a further cap-shaped disc 7i with a single central hole. This disc is not an impactor stage but serves solely as the collection plate for stage 7h. An O-ring, 12, is positioned within a circumferential recess in the base of each stage and is compressed to seal between each stage by the comression force transmitted from the inlet housing through spring 13, to the edge of the entry. It will be seen that, after the entry, the sampled gas is constrained to flow within volumes defined entirely by the stages, and all the air-borne dust particles which enter the entry aperture are deposited upon separately weighable parts. The gas exit holes are progressively narrowed in order to deposit specific size fractions of dust particles on the areas of impingement of the succeeding stage. A filter, 14, consisting of a conventional gas filter paper supported on a mesh screen, is mounted between the final stage and an inward-turned lip and held in position by an annular ring, 15. A connector, 16, is mounted downstream of the filter and provides a push on connection to a tube 19 from a conventional gas sampling pump 20 operating at a continuous 2 l/min.

Each stage is sprayed with an aerosol silicone grease which acts to retain particles of dust which have impinged; a mask is used for each stage to limit the coverage of the grease spray to the impingement area of each disc portion. After overnight "conditioning" or storage in conventional manner, each stage, the entry and the filter is weighed and the stack of stages is assembled and inserted within the cascade impactor body. The stack is held just free of contact with the cylindrical body by the O-rings. The entry and inlet housing are fitted and the spectrometer is attached to a wearer's clothing, and his personal environment is sampled for an appropriate time, for example, for a working shift. After disassembly of the spectormeter, and overnight conditioning, reweighing of the stages, entry and filter provides information on the weight of dust in each cut of aerodynamic sizes. In a prototype spectrometer, the stages were designed to give 50% cut-off aerodynamic diameters of 20, 14, 10.7, 6.3, 4.9, 3.4, 1.7, 0.9 microns, with the filter collecting all the particles with aerodynamic diameters below 0.9 microns.

Additions of the masses of dust deposited in the entry and on the filter to those collected at each impactor stage gives a measure of the wearer's inspirable dust dose received. Calculation of the aerodynamic size distribution of that inspirable dust from the cascade impactor data then provides a means by which health related dust sub-fractions (e.g. tracheobronchial, respirable, etc.) can be determined.

We claim:

1. A personal inspirable dust spectrometer comprising an elongated casing having an inlet section and an outlet means arranged so that air flow through said casing is along a path generally parallel to the longitudinal axis thereof; said inlet section having an inlet aperture in a sidewall of the casing and an entry which, when worn on a human body, has an entry efficiency for airborne dust approximating that of the human head during inhalation, said entry comprising an aperture surrounded by a lip, said lip protruding through said inlet aperture so that the flow of entry air into said casing is generally perpendicular to said longitudinal axis, a multi-stage cascade impactor having an inlet and an outlet and having a series of stages each capable of collecting a subfraction of dust and each comprising a cup shaped body with a generally flat element and a peripheral wall and at least one air exit hole in the flat element, said stages being dismountably assembled so as the peripheral wall of one stage seals by contacting the flat element of the stage immediately before, and said at least one air exit hole from one stage is positoned to permit air flow to impinge on a part of the flat element of the succeeding stage, and said outlet means including means connected to the outlet of the impactor for drawing air through the entry and through the impactor.

2. A dust spectrometer as claimed in claim 1, wherein a filter is fitted between the outlet from the impactor and the means for drawing air.

3. A dust spectrometer as claimed in claim 1, wherein the inlet section comprises an inlet housing and said entry is dismountably held within said housing.

4. The dust spectrometer of claim 1 in whcih the lip surrounding the aperture projects outwardly from the sidewall by 1-2 mm.

5. The dust spectrometer of claim 1 in which each of said cup shaped bodies is of identical size and shape.

6. The dust spectrometer of claim 1 in which the flat element and peripheral wall of eah cup shaped body is integrally formed.

* * * * *